United States Patent [19]
Johnson et al.

[11] Patent Number: 5,609,642
[45] Date of Patent: Mar. 11, 1997

[54] TIBIAL TRIAL PROSTHESIS AND BONE PREPARATION SYSTEM

[75] Inventors: Chris E. Johnson; Tim Vendrely, both of Memphis, Tenn.; Leo A. Whiteside, Bridgeton, Mo.; Thomas A. Carls, Memphis, Tenn.; John Steele, Aurora, Colo.; Khosrow Naraghian, Memphis, Tenn.

[73] Assignee: Smith & Nephew Richards Inc., Memphis, Tenn.

[21] Appl. No.: 389,100

[22] Filed: Feb. 15, 1995

[51] Int. Cl.⁶ ........................................................ A61F 2/38
[52] U.S. Cl. ............................................................ 623/20
[58] Field of Search ................................. 623/20; 606/88

[56] References Cited

U.S. PATENT DOCUMENTS

| | | | |
|---|---|---|---|
| 4,938,769 | 7/1990 | Shaw | 623/20 |
| 5,489,311 | 2/1996 | Cipolletti | 623/20 |

*Primary Examiner*—Randy C. Shay
*Attorney, Agent, or Firm*—Pravel, Hewitt, Kimball & Krieger

[57] ABSTRACT

The method of implanting a femoral and a tibial knee prosthesis and instruments for surgically implanting the femoral and tibial prosthesis component as disclosed. The method includes the formation of a plurality of surgical cuts on the patient's distal femur. A trial tibial prosthesis is then fitted to the surgically prepared distal femur. The trial prosthesis has a femoral articulating surface and a non-articulating surface that fits the patient's distal femur at the surgical cuts. A surgeon then forms a transverse cut on the patient's proximal tibia. The surgeon places a tibial trial prosthesis on the patient's proximal tibia, the trial prosthesis including a tibial trial stem that fits the patient's intramedullary canal, a tibial trial metallic tray or plate, and a plastic trial insert that fits the tibial tray or plate. The plastic insert includes a tibial articulating surface that can articulate with the femoral articulating surface. The respective articulating surfaces are placed in contact and the surgeon then moves the patient's knee through a full range of motion. During this movement of patient's knee through a full range of motion, the surgeon uses a lever that is attached to the trial tibial prosthesis to rotate the trial tibial prosthesis about its stem. The surgeon can try different rotational positions of the tibial trial prosthesis each time moving the knee through a full range of motion to ensure proper orientation and an accurate fit.

13 Claims, 7 Drawing Sheets

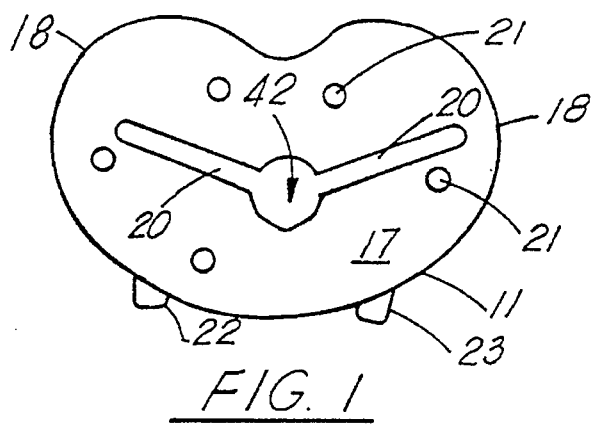
FIG. 1
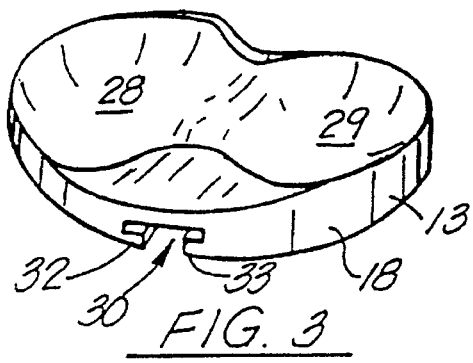
FIG. 3
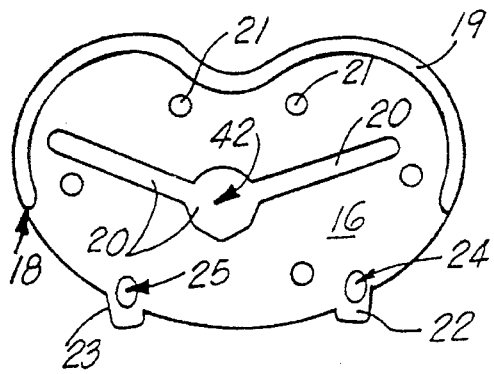
FIG. 2
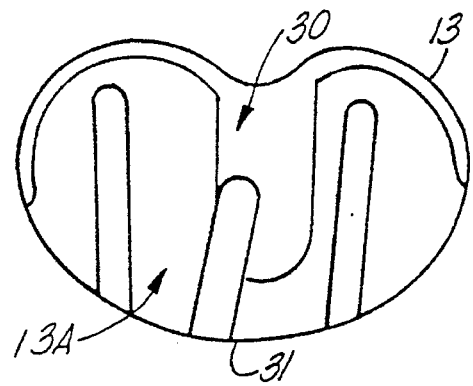
FIG. 4
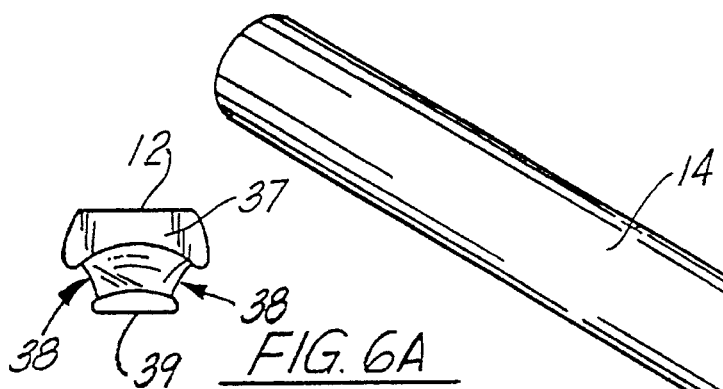
FIG. 5
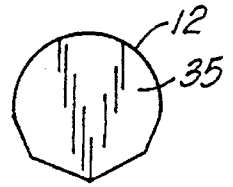
FIG. 6B
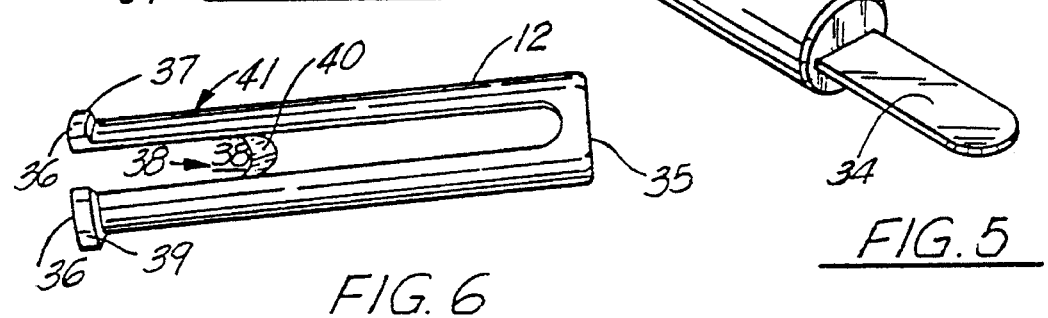
FIG. 6A
FIG. 6

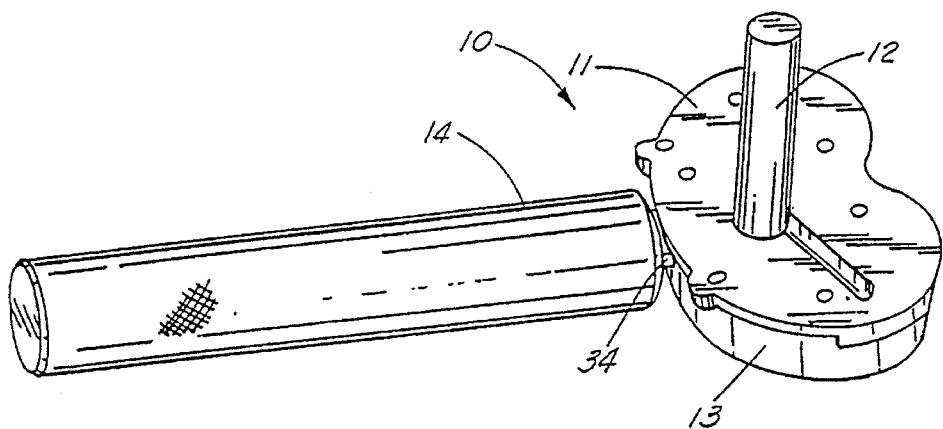
FIG. 7
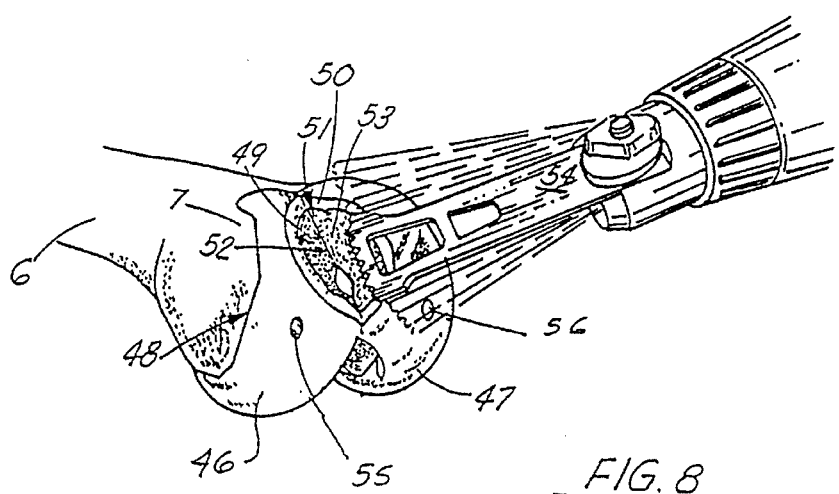
FIG. 8
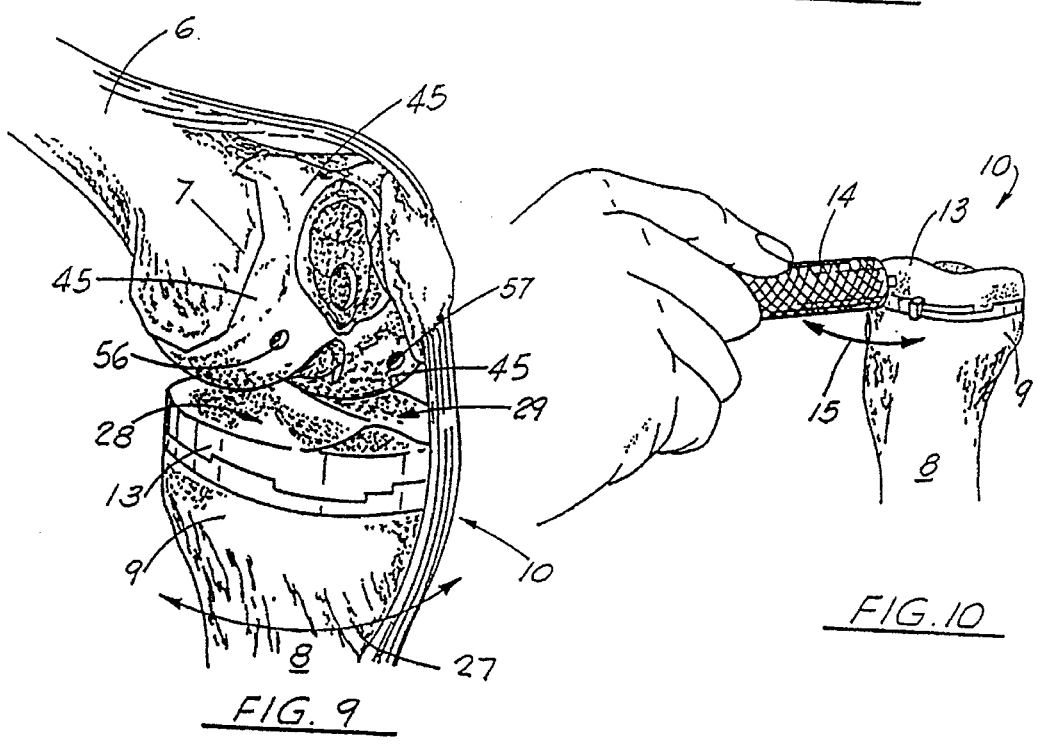
FIG. 9
FIG. 10

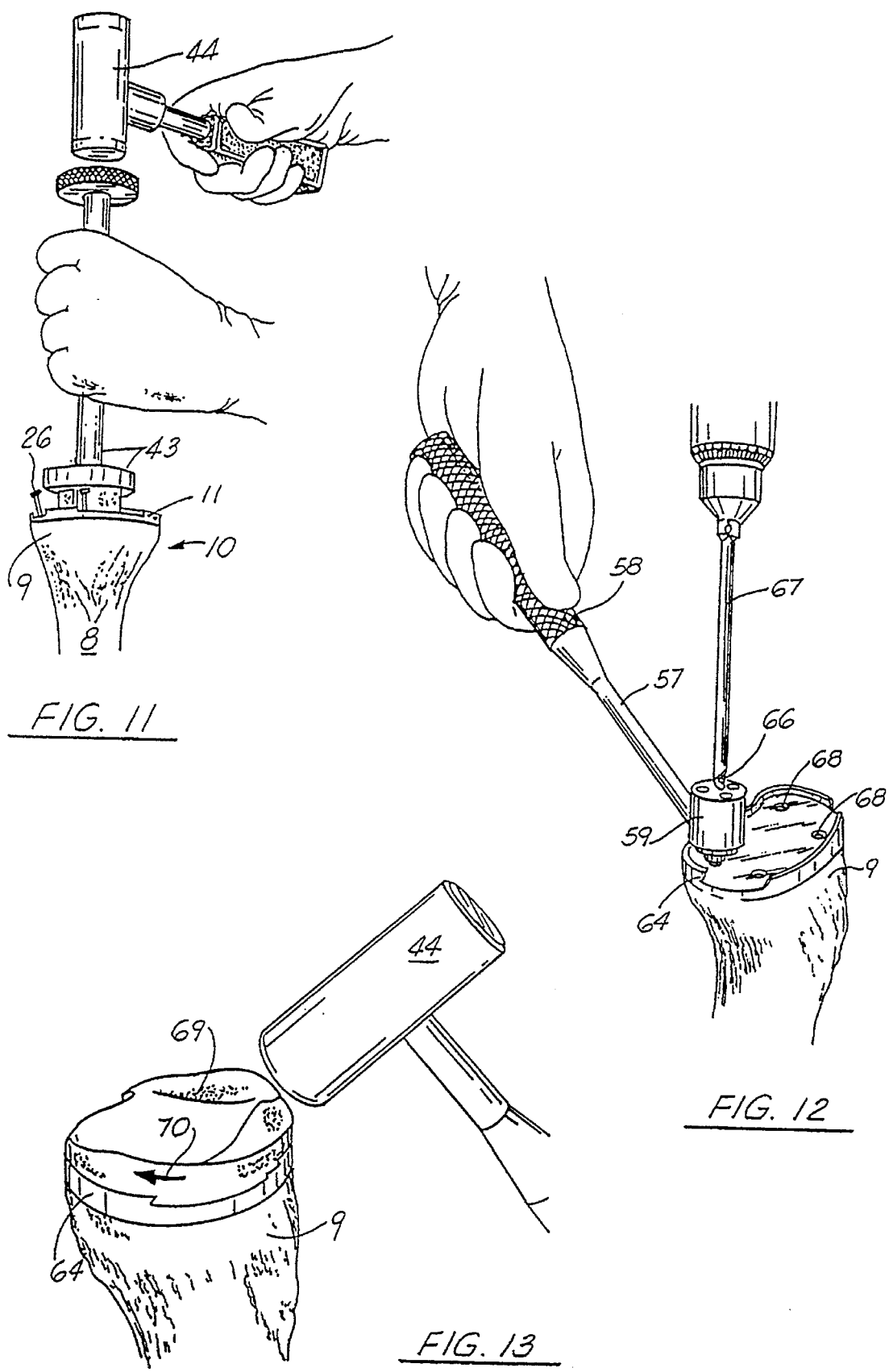

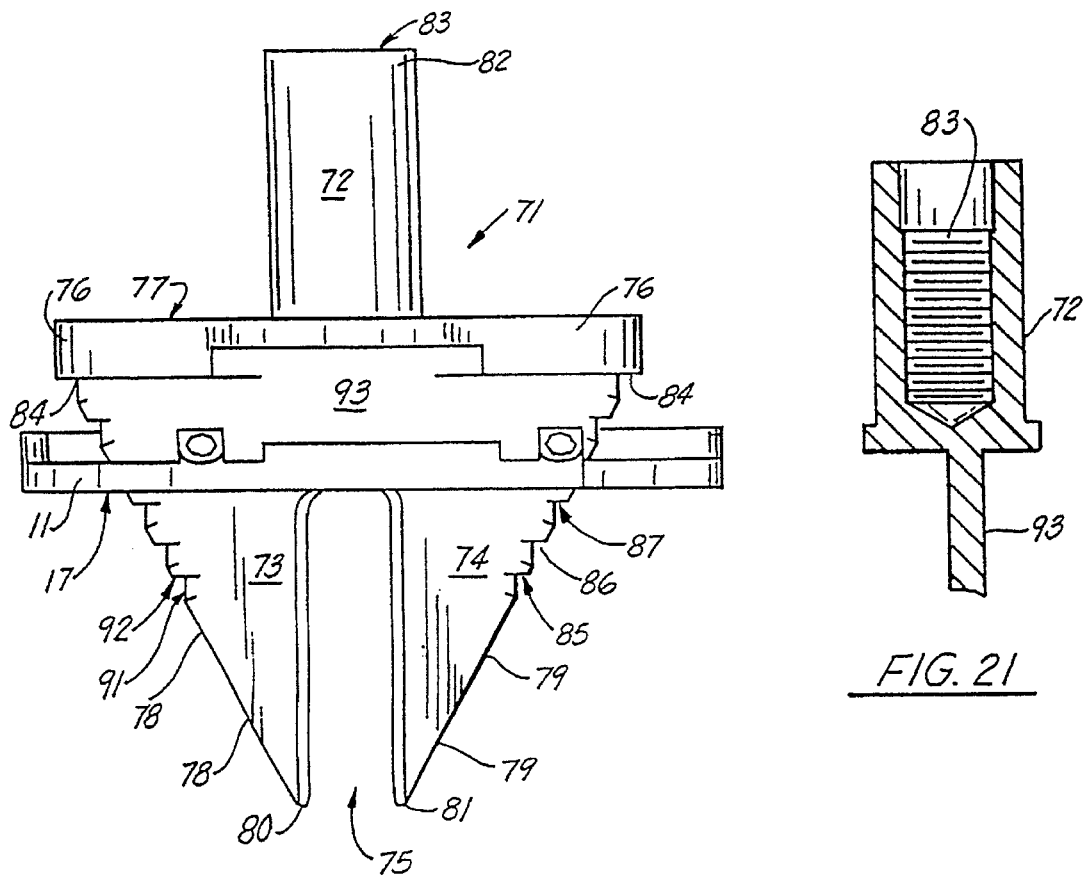
FIG. 18
FIG. 21
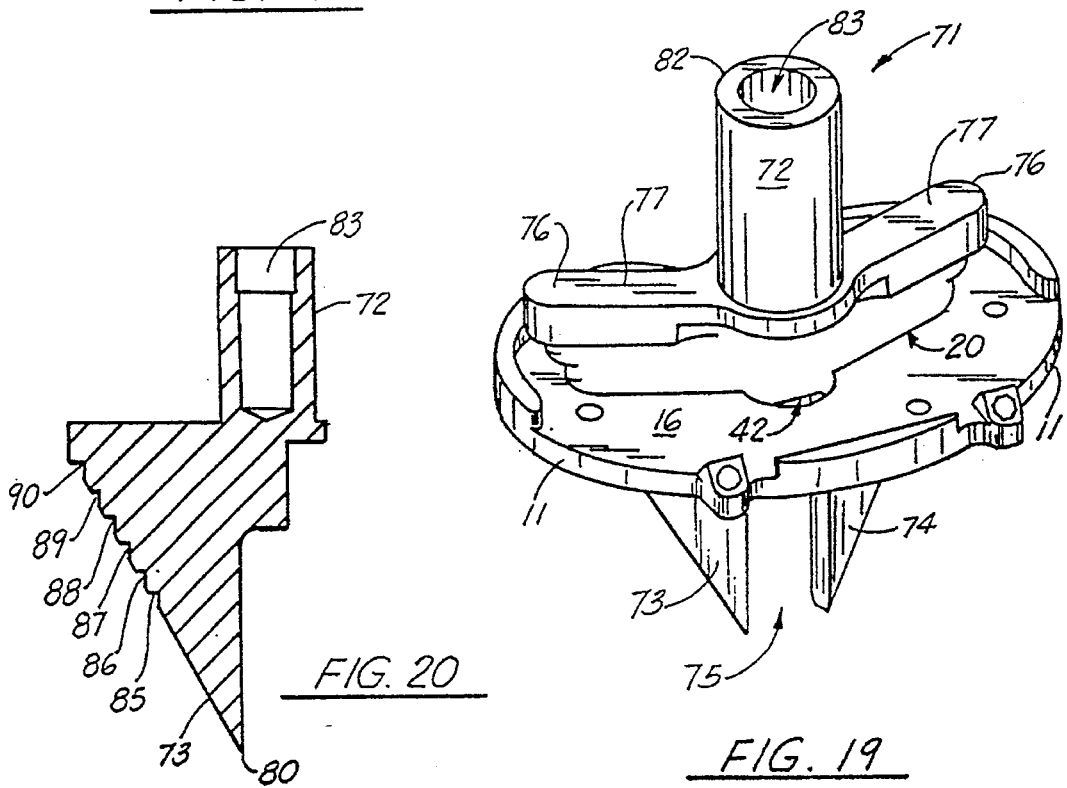
FIG. 20
FIG. 19

TIBIAL TRIAL PROSTHESIS AND BONE PREPARATION SYSTEM

BACKGROUND OF THE INVENTION

1. Field of the Invention

The present invention relates to orthopedic surgical instruments and surgical methods and more particularly relates to an improved method and apparatus for installing a knee prosthesis with instrumentation that allows a surgeon to rotate a tibial trial prothesis about the patient's intramedullary canal axis with a lever while the patient's knee is flexed through a full range of motion and with a corresponding femoral trial prosthesis in place.

2. General Background

In knee joint replacement surgery, a surgeon typically affixes two prosthesis components to the patient's femur and tibia. These replacement components are typically known as the femoral component and the tibial component.

The femoral component is placed on a patient's distal femur after the surgeon makes a plurality of surgical cuts. One common type of femoral prothesis has a J-shape. A femoral prosthesis is usually metallic, having a highly polished outer femoral articulating surface.

A common type of tibial prosthesis uses a laterally extending tray that is shaped to conform to the patient's proximal tibia after the proximal tibia has been cut transversely by the surgeon. The tibia prosthesis also includes a stem or plug that extends generally perpendicular to the tray and from the center of the tray. The stem is placed in a surgically formed opening that extends into the patient's intramedullary canal from the transverse cut formed on the proximal tibia.

A plastic, polymeric insert is attached to the tibial tray. This insert provides a tibial articulating surface that articulates with the femoral articulating surface as the patient's tibia moves through a full range of motion with respect to the patient's femur.

One of the problems with knee joint replacement surgery is that of accurately fitting the patient. Each patient has a different bone structure and geometry. Even though the surgeon uses x-rays to study a particular patient's anatomy at the knee, the surgeon does not have a perfect appreciation of the patient's anatomy until after the knee has been surgically exposed and the surgeon begins to make cuts on the femur and the tibia.

Knee prosthetic components are not available in infinite sizes. The surgeon must examine the patient's anatomy, make the requisite surgical cuts and install prosthesis components that fit.

A number of tibial components have been patented that relate to tibial components having a tray, a plastic insert with articulating surface, and a stem portion that provides initial fixation when the prosthesis is implanted. Other patents have issued that relate to cutting instrumentation for preparing the patient's proximal tibia to receive a tibial prosthetic insert as part of knee joint replacement surgery.

The Murray U.S. Pat. No. 4,016,606 discloses a knee prosthesis that includes a tibial component with a tray and with a stem adapted to be received in a longitudinal bore in the patient's femur. The stem has one end that is integral with a depending generally spheroidal surface having generally the same radius as the radius of the spheroidal depression in the insert.

In the Chiarizzio U.S. Pat. No. 4,601,289 there is disclosed a femoral trial prothesis/rasp assembly used in hip implant surgery. The assembly includes a handle that grips the combination trial prothesis/rasp in a secure manner by clamping over and locking on to a post on the trial prothesis/rasp which later serves as a mounting piece for a femoral prothesis head used in trial reductions.

A modular tibial prosthesis is disclosed in the Shaw U.S. Pat. No. 4,938,769. The Shaw patent discloses a tibial prosthesis for use during a total knee arthroplasty procedure which includes a modular two part tibial component comprising an in-bone anchorage assembly to which is removably attached a tibial tray adapted to receive and retain a bearing insert. Removal of the tray permits access to the interface between the bone and anchorage assembly in the event removal or revision are necessary. In preferred embodiments, the invention affords hybrid fixation of the tibial prosthesis in that bone cement for immediate fixation and adaptation for longer term bone ingrowth are featured. Shaw also discusses the use of porous coatings to enhance fixation.

U.S. Pat. No. 4,938,769 issued to James Shaw discloses an end bone anchorage assembly for a tibial prosthesis that includes an axially elongated central stem and a plurality of elongated fixation pegs spaced from the stem. The stem and the pegs have proximal and distal ends. The proximal ends of the stem define an attachment table. A plurality of structural links interconnect the pegs and the stem. Means is provided for removably attaching a tibial tray to the assembly wherein each of the pegs is connected to the stem by the structural link.

A tibial component for a replacement knee prosthesis is disclosed in the Lawes et al. U.S. Pat. No. 5,080,675. Lawes discloses a tibial component for a replacement knee prosthesis comprising a tibial tray for connection to a suitably prepared tibia, the tray carrying fixed lateral and medial condylar bearing components. Only the medial component has a shock absorber located beneath it.

U.S. Pat. No. 5,137,536 issued to Tomihisa Koshino describes a tibial component for an artificial knee joint. The tibial component includes a plate section having an upper surface and a pair of bearing surfaces parts that are adapted to be in sliding contact with a femoral component. A stem portion extends downwardly from a lower surface of the plate section. A pair of blade like members extend obliquely and posteriorly from the stem. The plate section has a lower surface with a plurality of elongated grooves for improving affinity with respect to the surrounding bone, the grooves including a first group of grooves and a second set of group of grooves extending perpendicularly to the first group of grooves.

An example of a modular tibial support is seen in the Elias U.S. Pat. No. 5,246,459 entitled "Modular Tibial Support Pegs for the Tibial Component of a Prosthetic Knee Replacement System". The Elias Patent discloses a modular tibial support peg operable to secure a tibial component of a knee joint prosthesis to a tibia having a groove. The modular tibial support peg includes a cylindrical body with a ridged outer surface operable to engage the groove in the tibia. The modular tibial support peg further includes a plurality of spikes extending inferiorly from the cylindrical body. The spikes are operable to engage the tibia at the inferior end of the groove.

SUMMARY OF THE INVENTION

The present invention provides an improved method and apparatus for implanting femoral and tibial prosthesis components. The surgeon first forms a plurality of cuts on the patient's distal femur and fits a femoral trial prosthesis to the surgically prepared distal femur. The femoral trial prosthesis has an articulating surface for engaging a corresponding surface of a tibial prosthesis. The femoral trial also has a non-articulating surface that fits the patient's distal femur at the surgical cuts.

The surgeon forms a transverse cut on the patient's proximal tibia. A tibial trial prosthesis is then assembled from a plurality of components of different shapes and sizes. The tibial trial prosthesis is formed of a trial tibial stem, a trial tibial tray or plate and a trial plastic insert.

In the method of the present invention, a plurality of trays, a plurality of stems, and a plurality of plastic inserts are provided so that the surgeon can custom construct a trial prosthesis with these plurality of trial tibial prosthesis components.

Each of the plastic inserts has a tibial articulating surface that articulates with the femoral articulating surface of the trial femoral prosthesis.

During the surgery, the surgeon can place the femoral articulating surface against the selected tibial trial prosthesis articulating surface so that fit can be viewed before the actual prosthesis components (i.e. tibial and femoral) are implanted. The surgeon can then move the patient's knee joint through a full range of motion during which the femoral and tibial articulating surfaces of the corresponding trial prosthesis components articulate with each other. With the present invention, the surgeon can adjust the relative rotational positions of these trial components before the final positions are fixed.

An instrument (preferably a lever with a handle) is provided for rotating the tibial trial prothesis about its trial stem so that articulation of the femoral trial prothesis and the tibial trial prosthesis can be observed. The surgeon can observe the fit between the trial tibial and trial femoral prosthesis as the surgeon moves the patient's knee through a full range of motion, and as the surgeon rotates the trial prosthesis into different rotational positions to obtain the best fit.

Using the method and apparatus of the present invention, the surgeon can build a custom "trial" tibial prosthesis to fit the patient's anatomy and then exactly position the tibial trial prosthesis in a desired rotational position after repeatedly rotating the knee through a full range of motion. In using the method of the present invention, an optimum fit is obtained. This method obtains correct orientation of the knee prosthesis through a full range of motion.

Once the surgeon determines that correct orientation of the components, the surgeon can pin both the femoral trial prothesis and the tibial trial prosthesis to the underlying bone tissue.

The femoral trial prosthesis has openings that allow the surgeon to drill into the underlying tissue. Those openings receive pegs of the final actual femoral prosthesis component after the trial prosthesis is removed. The surgeon rotates the tibial trial prosthesis until it is in an optimum position. The surgeon then pins the tibial trial prosthesis in position. The surgeon can remove the articular insert trial exposing the tibial prep-plate. The surgeon the marks the tibia below the alignment marks on the tibial prep-plate. When using a non-porous implant, the surgeon can remove the articular plastic insert trial and prepare for the distal fins on the implant using an appropriately sized fin punch. If a long stem is desired, the surgeon can then ream up to the stem diameter.

The surgeon places the tibial implant using marks that were made on the tibia when the trial prosthesis was in position, or using the cut made by the fin punch. The fin punch is "stepped" to correspond to different prosthesis sizes. The tibial prosthesis is installed using a tibial impactor to seat the tibial implant on the proximal tibia. The surgeon can use screws or cement to fasten the final selected tibial component to the proximal tibia.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is bottom view of the tibial prep-plate portion of the preferred embodiment of the apparatus of the present invention;

FIG. 2 is a top view of the tibial prep-plate portion of the preferred embodiment of the apparatus of the present invention;

FIG. 3 is a perspective view of the articular insert trial portion of the preferred embodiment of the apparatus of the present invention;

FIG. 4 is a bottom view of the articular insert trial portion of the preferred embodiment of the apparatus of the present invention;

FIG. 5 is a perspective view of the articular insert trial rotation handle portion of the preferred embodiment of the apparatus of the present invention;

FIG. 6 is a perspective view of the stem plug portion of the tibial trial insert portion of the preferred embodiment of the apparatus of the present invention;

FIG. 6A is a top view of the plug of FIG. 6;

FIG. 6B is a bottom view of the plug of FIG. 6;

FIG. 7 is a schematic perspective view illustrating the trial tibial prosthesis and the trial rotation handle portions of the preferred embodiment of the apparatus of the present invention;

FIG. 8 is a schematic perspective view illustrating a resection of the patella femoral groove, cutting along the medial and lateral sides of the femoral trial;

FIG. 9 illustrates the trial femoral prosthesis and the trial tibial prosthesis installed respectively on the patient's distal femur and proximal tibia and prior to rotation to the tibial trial prosthesis;

FIG. 10 is a schematic view illustrating rotation of the trial tibial prosthesis;

FIG. 11 is a schematic view illustrating a preparation of the proximal tibia to receive distal fins of a tibial implant using a fin punch;

FIG. 12 is a perspective view illustrating preparation for bone screws for the tibial tray;

FIG. 13 is a schematic perspective view illustrating attachment of the plastic insert of the tibia prosthesis to the tibial tray;

FIG. 18 is an elevational view of the preferred embodiment of the fin punch portion of the preferred embodiment of the apparatus of the present invention;

FIG. 19 is a perspective view illustrating the fin punch portion of the preferred embodiment of the apparatus of the present invention;

FIG. 20 is a fragmentary sectional view illustrating the fin punch of FIGS. 18–19;

FIG. 21 is another fragmentary sectional view illustrating the fin punch of FIGS. 18–19;

DETAILED DESCRIPTION OF THE PREFERRED EMBODIMENT

Figure 14:
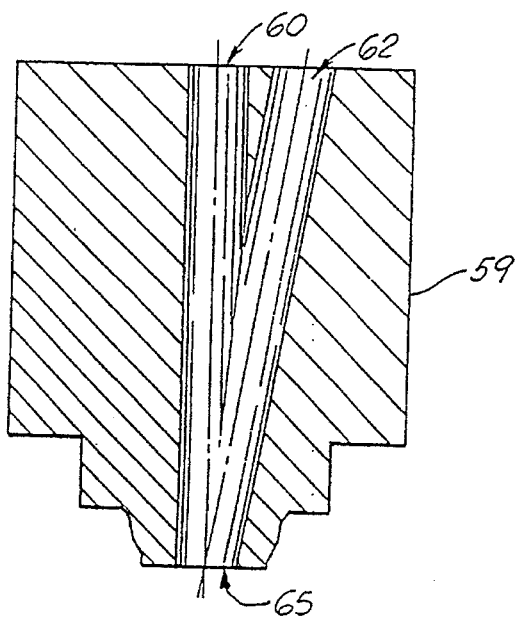
FIG. 14 is a partial sectional view of the tibial screw guide portion of the preferred embodiment of the apparatus of the present invention.
Figure 15:
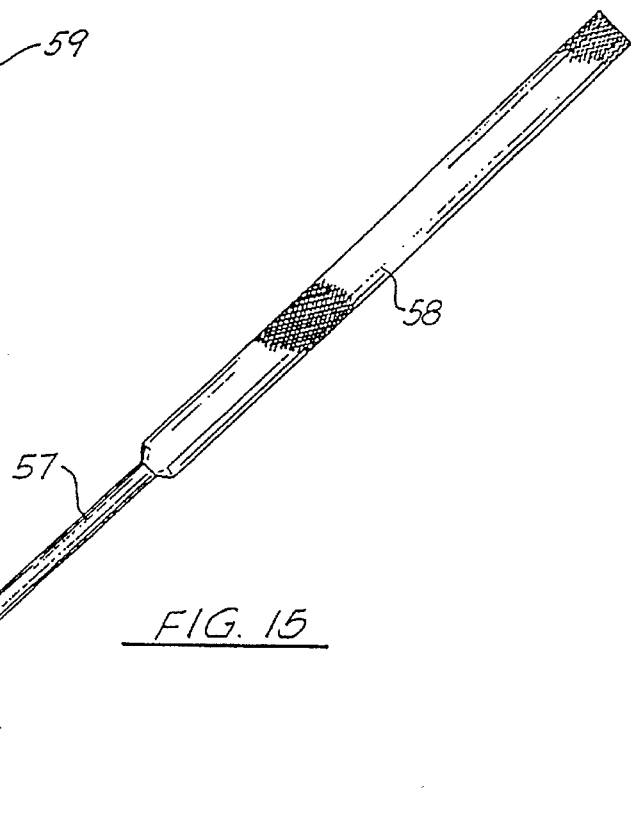
FIG. 15 is an elevational view of the tibial screw drill guide portion of the preferred embodiment of the apparatus of the present invention.
Figure 16:
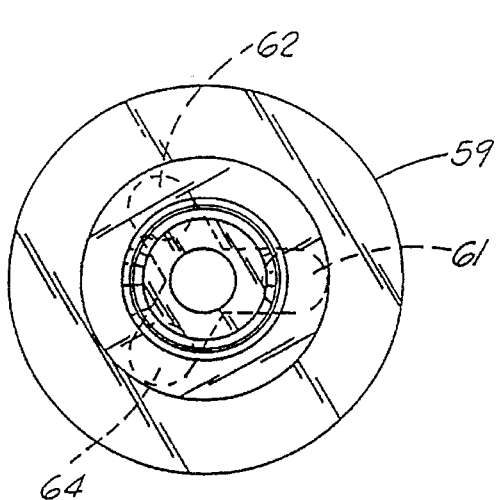
FIG. 16 is a partial bottom view of the tibial screw drill guide portion of the preferred embodiment of the apparatus of the present invention.
Figure 17:
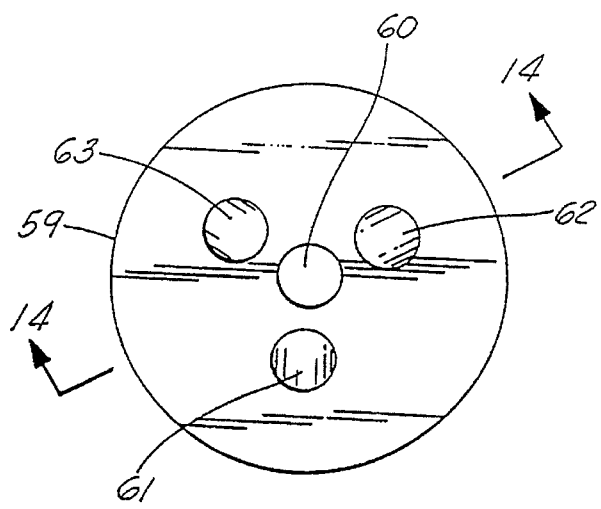
FIG. 17 is a partial top view of the tibial screw drill guide portion of the preferred embodiment of the apparatus of the present invention.

FIGS. 1–4 and 7 show generally the preferred embodiment of the tibial trial prosthesis of the present invention designated by the numeral 10 in FIG. 7. Trial tibial prosthesis 10 is comprised of tray 11, stem or plug 12, and plastic insert 13. The entire trial prosthesis 10 can be rotated after assembly and surgical placement on the patient's distal tibia 9 (see arrow 15 in FIG. 10.)

FIGS. 1–2 show trial tray or plate 11. Tray 11 includes an upper surface 16 and a lower surface 17. A shoulder portion 19 extends partially about the periphery 18 at the posterior of tray 11. A central V-shaped slot 20 is provided for allowing a fin punch 43 to be used to make surgical cuts in the proximal tibia corresponding to fins that are a permanent part of the final tibial prosthesis to be implanted. In FIG. 11, the surgeon uses mallet 44 to drive fin punch 43.

The fin punch 43 is used after the tibial trial prosthesis 10 has been finally correctly oriented using the method of the present invention. Central opening 42 receives plug 12. Shoulders 37, 39 extend beyond the periphery of opening 42. Plug 12 has proximal 36 and distal 35 ends. A plurality of openings 21 can be provided in tray 11 for drilling holes that will determine the position of bone screws that hold the final tibial prosthesis to proximal tibia 9. A preferred embodiment of the fin punch will be described more full hereinafter.

A pair of spaced apart appendages 22, 23 extend away from the periphery 18 of tray 11. The appendages 22, 23 (see FIGS. 1–2) have angled openings 24, 25 for receiving bone spikes 26 (See FIG. 11). The openings 24, 25 are circular in cross section to conform to the outer surface of bone spikes 26. Each opening 24, 25 forms an acute angle with bottom surface 17 of tray 11. This allows the surgeon to pin the trial prosthesis 10 to the patient's proximal tibia 9 after rotation has been accomplished using the lever 14 to determine the best fit of tray 11 on proximal tibia 9. Bone spikes 26 placed through the angled openings 22, 23 fix the position of the tray 11 with respect to the patient's proximal tibia 9 during punching of the V-shaped opening in the patient's proximal tibia using a fin punch 43 (see FIG. 11).

In FIGS. 3–4, plastic trial insert 13 is shown. The insert 13 has a pair of concavities 28, 29 that define articulating surfaces that fit and articulate with condylar portions of a femoral trial prosthesis 45 mounted on the distal end 7 of the patient's femur 6 as shown in FIG. 9.

A horizontal slot 30 extends from the periphery 18 of insert 13 toward the center thereof. Slot 30 is generally parallel to the generally flat underside 13A of insert 13, generally parallel thereto slot 13 is positioned in between underside 13 and articulating surfaces 28, 29 as shown.

As shown in FIG. 4, the slot 30 terminates before reaching the anterior side 31 of insert 13. A pair of annular shoulders 32, 33 retain the lever tab 34 at one end of line 14, and more particularly the tab end 34 thereof so that rotation of the lever 14 also rotates the insert 13, the tray 11, and the plug or stem 12 to which tray 11 is affixed. In FIG. 10, the entire assembly of tray 11, insert 13, and stem 12 are seen being rotated as illustrated by the curved arrow 15. Tab 34 can be used to engage and manipulate insert 13. Thus, lever 14 and its tab 34 can be used to aid in removal of insert 13 from tray 11, or in attaching insert 13 to tray 11.

In FIG. 6, 6A and 6B, the trial stem 12 provides a distal end 35 that is shaped to conform to the transverse cross section of opening 42 (see FIG. 6A) and proximal end 36. The proximal end 36 has a pair of spaced apart shoulders 37, 39 that extend away from the central longitudinal axis of the stem. Shoulders 37, 39 define a means of engaging the stem 12 at top surface of the tray 11 upon assembly when the surgeon is building a trial prosthesis.

The shoulders 37, 39 extend beyond the outer surface 41 of stem 12 and thus beyond the central opening 42 in tray 11. The slot 38 between shoulders 37, 39 allows the fin punch to fit between the shoulder 37, 38. Slot 38 is positioned between the laterally extending shoulders 37, 39. The slot 38 extends only about halfway along the length of the trial stem, terminating at surface 40.

In FIG. 8, the trial femoral prosthesis 45 is shown affixed to the patient's distal femur 7. The distal femur is surgically prepared with anterior and posterior flat cuts that are parallel, a distal cut that is perpendicular to the anterior and posterior cuts, and chamfer cuts (anterior and posterior) that extend diagonally respectively between the distal cut and the anterior and posterior cuts. Such a surgical preparation of the distal femur 7 to receive a femoral prosthesis, or trial femoral prosthesis is known in the art.

The trial femoral prosthesis 45 of the present invention has a pair of curved articulating condylar surfaces 46, 47.

The rear surface 48 of trial femoral prosthesis 45 is sized and shaped to fit the surgically prepared distal femur 7. Trial femoral prosthesis 45 has a pair of flat cutting guide surfaces 49, 50 that allow the surgeon to form surgical cuts 52, 53 forming a V-shaped recess in the patient's distal femur 7. Blade 54 in FIG. 8 is seen resecting the distal femur 7 with cuts 52, 53 to form recess 51. The formed recess 51 allows placement of a final femoral prosthesis.

In FIGS. 9–10, trial tibial prosthesis 10 has been installed by the surgeon on the patient's proximal tibial 9. The surgeon has also installed a trial femoral prosthesis 45 on the distal femur 7.

Using the method and apparatus of the present invention, the surgeon can determine the best fit for the tibial trial prosthesis 10 in relation to the trial femoral prosthesis 45. Trial femoral prosthesis 45 (FIG. 8) can be drilled at openings 55, 56 and affixed to the distal femur 7 using bone screws or pegs. These openings 55, 56 can also define the position of pegs that attach the final femoral prosthesis to the distal femur 6.

In FIG. 10, the trial prosthesis 10 is shown mounted on the patient's proximal tibia 9. Lever 14 fits slot 30 of the trial prosthesis insert 13. Using the lever 14, the surgeon can now rotate the trial prosthesis 10 about its stem portion 12, as shown by the curved arrows 15 in FIG. 10. This can be done as the surgeon rotates the knee through its full range of motion to obtain the best fit.

The surgeon rotates the lever 14 to place the trial prosthesis 10 in a desired position (see FIG. 10). The surgeon can also rotate the tibia relative to the femur (see arrow 27 in FIG. 9) through a full range of motion. If the surgeon is not satisfied with the fit, the lever 14 can be used to reposition the trial prosthesis 10, and rotate the knee again through a full range of motion. The lever 14 and its tab 34 can also be used to change inserts 11, such as a different size or different thickness insert 11. The procedure can be repeated until the surgeon is completely satisfied with the orientation of trial prosthesis 10 in relation to trial femoral prosthesis 45.

In FIGS. 12 and 14–17, there can be seen screw drill guide 57. The drill guide 57 can be used to install a final tibial prosthesis 64 on the patient's proximal tibia 9 once the surgeon has decided upon a particular size and shape of tibial implant 64 based upon the use as aforedescribed of the tibial trial prosthesis 10. Drill guide 57 includes a handle 58 for holding and manipulating the drill guide 57.

A guide sleeve 59 is generally cylindrically shaped, and provides a plurality of bores through bone screws can be placed for attaching the final tibial prosthesis 64 to the patient's proximal tibia 9. Guide sleeve 59 preferably includes four (4) screw guide bores. A straight bore 60 tracks the central longitudinal axis of guide sleeve 59. A plurality of angles bores 61–63 extend from the upper surface to the lower surface of the guide sleeve 59, all of the bores 61–63 exiting at common opening 65.

In FIG. 12, there can be seen a drill 66 being guided by the surgeon through one of the bores 60–63 of the guide sleeve 59. The drill 66 is simply placed in the desired bore 60–63 and driven into one of the openings 68 of the tibial prosthesis 64 using drill driver 67. The surgeon inserts a bone screw through the prepared hole then places the final plastic insert 69 on the prosthesis 64 and hammers it into place using mallet 44, hammering in the direction of arrow 70.

FIGS. 18–21 illustrate the all poly plastic fin punch of the present invention designated generally by the numeral 71. In FIGS. 1–2, fin punch 71 has a cylindrical section 72 with a pair of blades 73, 74 joined at vertical plate 93 and extending downwardly with respect to the central axis of the cylindrical section 72. A horizonal frame section 76 forms a connection between the cylindrical sections 72 and the pair of blades 73, 74. A generally U-shaped slot 75 is positioned between the blade member 73, 74.

The horizontal section 76 has a generally flat upper surface 77. Each of the blades 73, 74 provides a respective inclined cutting edge 78, 79. The cutting edge 78 begins at pointed distal end 80 and extends to horizontal surface 84 of section 76. The inclined cutting edge 79 begins at pointed distal end 81 of blade 74 and extend to horizontal surface 84 of section 76. A plurality of notches or stepped portions 85–90 can be seen along each of the inclined cutting surfaces 78, 79 of the blades 73, 74.

Each of the stepped portions 85, 90 includes a vertical surface 91 and a horizonal surface 92. The step portions combined with the size of slot 20 of trial tray 11 to limit the depth of cut that is made by the fin punch 71. The punch 71 only goes down to that particular stepped portion or notch 85–90 that can be fitted through the slot 20 depending upon the width of the slot 20. For example, the punch 71 only goes down to the fourth notch for a size "4" tibial prep-plate 11 because the slots 20 in the trial plate 11 for a size "4" or a given distance wide. They would be provided as wider slots 20 for example on sizes "5" and "6". The slot 20 would be smaller for an over all width for a size "3" or smaller. This sizing concept also corresponds to the implant design since the fins or blades 73, 74 get larger in width the larger the size.

FIGS. 22–32 illustrate tibial trial prosthesis 94 that can be used with a tibial prep plate tray 95. For purposes of the embodiment of FIGS. 22–32, prep plate tray 95 can be assumed to have the same configuration and structure as tray 11 described in FIGS. 1 and 2.

Figure 22:
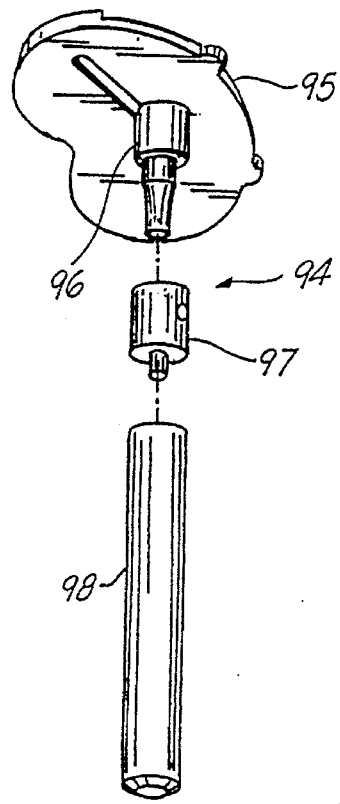
FIG. 22 is a perspective view of a second embodiment of a tibial trial prosthesis.
Figure 23:
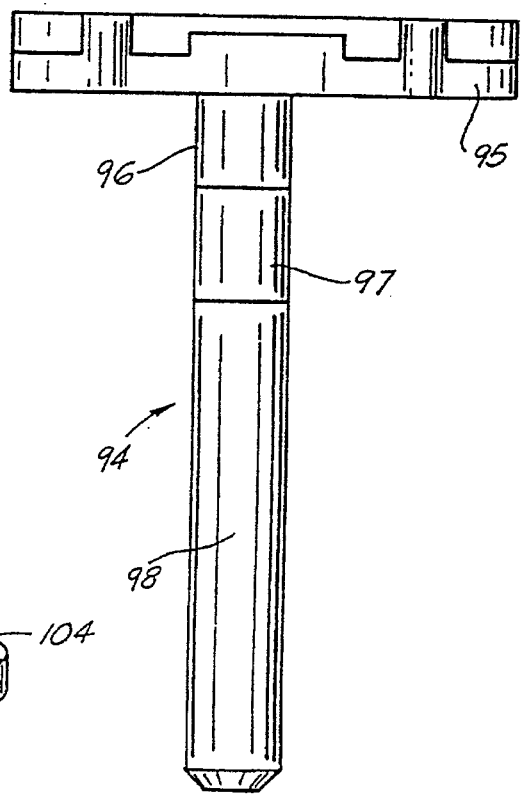
FIG. 23 is an elevational view of a second embodiment of the tibial trial prosthesis.

FIGS. 22–23 show generally the second embodiment of the tibial trial prosthesis designated generally by the numeral 94. Tibial trial prosthesis 94 includes a prep plate or tray 95 that is attached to trial taper 96, trial stem coupler 97 or 97A, and trial stem 98.

Figure 24:
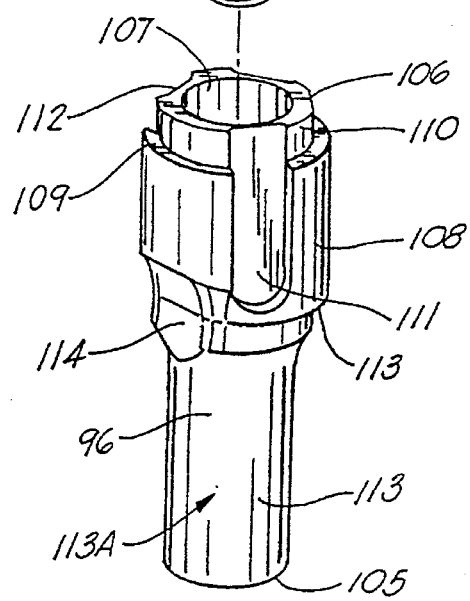
FIG. 24 is an exploded perspective view of the trial taper portion of the second embodiment of the tibial trial prosthesis.

The trial taper 96 is shown generally in FIG. 24. Trial taper 96 includes a generally cylindrical bushing 99 having an enlarged integral head portion 100. An assembly bolt 101 can be placed through counterbore 104 of bushing 99. The counterbore 104 is shaped to retain the head 103 of bolt 101, allowing only the threaded section 102 to pass therethrough as shown in FIG. 24. Bushing 99 and its enlarged head 100 are coupled to stem 113 that has a frustroconical surface 113A thereon at the lower distal 105 end portion.

The proximal 106 end of stem 113 provides a counterbore 107 that is sized and shaped to receive bushing 99 and the threaded portion 102 of bolt 101. Further, the counterbore 107 includes an internally threaded section for engaging the threads 102 of bolt 101 upon assembly. The bolt head 103 can have a hexagonal recess, for example, for accepting an allen wrench that impart torque to the bolt 101 during assembly to stem 113.

As with the trial tray 11 of FIGS. 1–2, a central opening 42 can be provided into plate 95. The opening 92 is sized and shaped to receive a reduced section 110 of stem 113 at proximal end 106 thereof. A thickened 108 section of stem 113 extends between annular shoulder 109 and frustroconical surface 113A. The thickened section 108 can carry a pair of longitudinally extending slots 111, 112 that receive the blades of fin punch 71. Thus, the trial plate can have a V-shaped slot as with the slot 20 on plate 11 of FIGS. 1–2.

After the bushing 99, bolt 101 and stem 113 have been assembled, the slot 20 extends away from stem 113 and the blades of fin punch 71 can pass on opposites sides of the trial taper 96.

Figure 25:
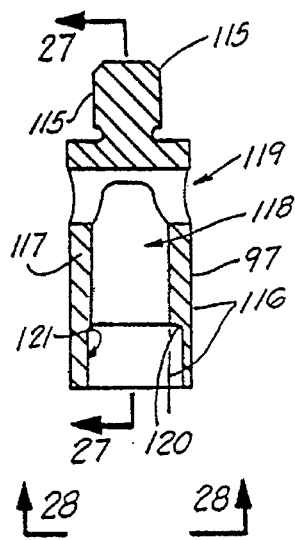
FIG. 25 is a fragmentary sectional view illustrating the trial stem coupler of FIGS. 22–23.
Figure 26:
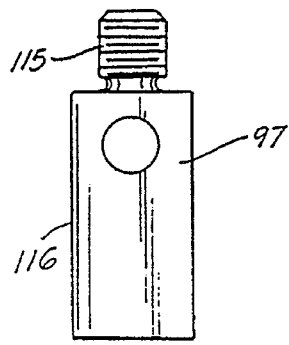
FIG. 26 is a elevational view of the trial stem coupler of FIGS. 22–23.
Figure 27:
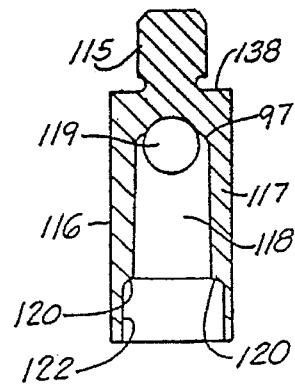
FIG. 27 is a fragmentary sectional view illustrating the trial stem coupler of FIGS. 22–23.
Figure 28:
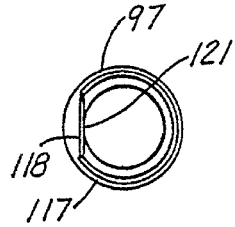
FIG. 28 is an end view illustrating the trial stem coupler of FIGS. 22–23.

A flat surface 114 on stem 113 cooperates with a similar flat surface of trial stem coupler 97, 98. In FIGS. 25, 28, a first trial stem coupler 97 is shown. In FIGS. 29–32, a second trial stem coupler 97A is shown that includes an angled bore.

In FIGS. 25–28, trial stem coupler 99 includes an externally threaded smaller diameter section 115 and a larger diameter cylindrical section 116 that is unthreaded. The section 116 provides a frustroconical bore 118 surrounded by a thick annular side wall 117 and a thin annular side wall 122. An annular shoulder 120 extends between the thick annular side wall 117 and the thin annular side wall 122. A transverse bore 119 extends at generally right angles to the frustroconical bore 118 as shown in FIG. 25. Flat surface 121 is positioned at thin annular side wall 122. The flat surface 121 mates with the flat surface 114 on stem 113 upon assembly of trial taper 96 and coupler 97.

In FIGS. 29–32, coupler 97A is shown having an internal inclined frustroconical bore 126. The coupler 97A includes an externally threaded smaller diameter section 123, a larger diameter unthreaded cylindrical section 124 surrounded by a thick annular wall 125 and a thin annular wall 130. As with the coupler 97, the coupler 97A includes a transverse bore 127. An annular shoulder 128 extends between the thick annular wall 125 and the thin annular wall 130. A flat surface 129 at thin annular surface 130 cooperates with a corresponding flat surface 114 on stem 113 upon assembly of trial taper 96 and the trial stem coupler 97A.

Figure 29:
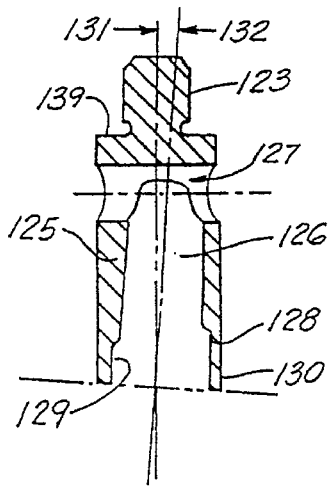
FIG. 29 is a fragmentary sectional view illustrating another trial stem coupler.
Figure 30:
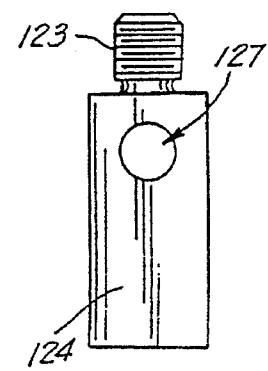
FIG. 30 is an elevational view of another trial stem coupler.

In FIG. 29, axis 131 represents a normal axis that is the central longitudinal axis of threaded cylindrical section 123. The axis 132 is an offset axis that is the central longitudinal axis of inclined frustroconical bore 126. The angle between the normal axis 131 and the inclined axis 132 can be, for example, between about 3 and 8 degrees.

Figure 31:
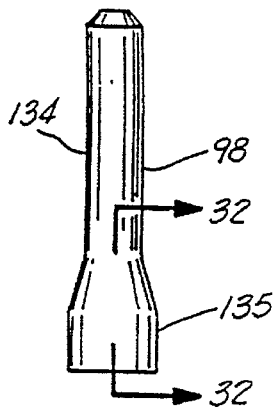
FIG. 31 is an elevational view of the trial stem of FIGS. 22–23.
Figure 32:
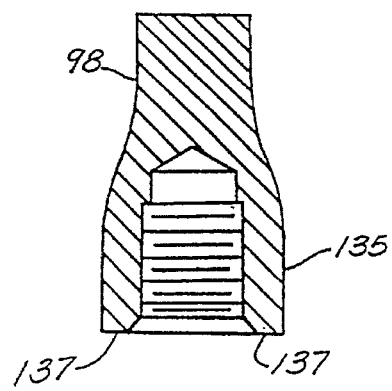
FIG. 32 is fragmentary section view of the trial stem of FIGS. 22–23.

In FIGS. 31–32, the trial stem 98. Trial stem 98 includes a lower frustroconically-shaped distal end 133, a generally cylindrically-shaped elongated section 134, and a thickened proximal end portion 135. The proximal end portion provides an internally threaded bore 136 that can form a connection with either the externally threaded section 115 of trial stem coupler 97 or the externally threaded section 123 of trial coupler 97A. Upon assembly, the flat annular surface 137 of proximal end portion 135 mates with the flat annular surface 138 of trial coupler 97 or the flat annular surface 139 of trial coupler 97A.

The following table lists the parts numbers and parts descriptions as used herein and in the drawings attached hereto.

| PARTS LIST | |
|---|---|
| Part Number | Description |
| 6 | femur |
| 7 | distal femur |
| 8 | tibia |
| 9 | distal tibia |
| 10 | trial prosthesis |
| 11 | tray |
| 12 | stem |
| 13 | insert |
| 13A | underside |
| 14 | handle |
| 15 | arrow |

| PARTS LIST -continued | |
|---|---|
| Part Number | Description |
| 16 | upper surface |
| 17 | lower surface |
| 18 | periphery |
| 19 | raised shoulder portion |
| 20 | V-shaped slot |
| 21 | opening |
| 22 | appendage |
| 23 | appendage |
| 24 | angled opening |
| 25 | angled opening |
| 26 | bone spike |
| 27 | arrow |
| 28 | concavity |
| 29 | concavity |
| 30 | slot |
| 31 | anterior side |
| 32 | shoulder |
| 33 | shoulder |
| 34 | tab |
| 35 | distal end |
| 36 | proximal end |
| 37 | shoulder |
| 38 | slot |
| 39 | shoulder |
| 40 | surface |
| 41 | surface |
| 42 | opening |
| 43 | fin punch |
| 44 | mallet |
| 45 | trial femoral prosthesis |
| 46 | condylar articulating surface |
| 47 | condylar articulating surface |
| 48 | rear surface |
| 49 | cutting guide surface |
| 50 | cutting guide surface |
| 51 | V-shaped recess |
| 52 | surgical cut |
| 53 | surgical cut |
| 54 | blade |
| 55 | opening |
| 56 | opening |
| 57 | screw drill guide |
| 58 | handle |
| 59 | guide sleeve |
| 60 | straight bore |
| 61 | angled bore |
| 62 | angled bore |
| 63 | angled bore |
| 64 | tibial prosthesis |
| 65 | common opening |
| 66 | drill |
| 67 | driver |
| 68 | opening |
| 69 | plastic insert |
| 70 | arrow |
| 71 | fin punch |
| 72 | cylindrical section |
| 73 | blade |
| 74 | blade |
| 75 | slot |
| 76 | horizontal section |
| 77 | flat surface |
| 78 | inclined cutting edge |
| 79 | inclined cutting edge |
| 80 | pointed distal end |
| 81 | pointed distal end |
| 82 | proximal end |
| 83 | internally threaded bore |
| 84 | horizontal surface |
| 85 | stepped portions |
| 86 | stepped portions |
| 87 | stepped portions |
| 88 | stepped portions |
| 89 | stepped portions |
| 90 | stepped portions |
| 91 | vertical surface |

PARTS LIST

| Part Number | Description |
| --- | --- |
| 92 | horizontal surface |
| 93 | vertical plate |
| 94 | tibial trial prosthesis |
| 95 | prep plate tray |
| 96 | trial taper |
| 97 | trial stem coupler |
| 97A | trial stem coupler |
| 98 | trial stem |
| 99 | bushing |
| 100 | head |
| 101 | bolt |
| 102 | threads |
| 103 | head |
| 104 | counterbore |
| 105 | distal end |
| 106 | proximal end |
| 107 | counterbore |
| 108 | thickened section |
| 109 | annular section |
| 110 | reduced section |
| 111 | longitudinal slot |
| 112 | longitudinal slot |
| 113 | stem |
| 113A | frustroconical surface |
| 114 | flat surface |
| 115 | externally threaded section |
| 116 | cylindrical section |
| 117 | thick annular side wall |
| 118 | frustroconical bore |
| 119 | transverse bore |
| 120 | annular shoulder |
| 121 | flat surface |
| 122 | thin annular side wall |
| 123 | externally threaded section |
| 124 | cylindrical section |
| 125 | thick annular wall |
| 126 | inclined frustroconical bore |
| 127 | transverse bore |
| 128 | annular shoulder |
| 129 | flat surface |
| 130 | thin annular wall |
| 131 | normal axis |
| 132 | inclined axis |
| 133 | distal end |
| 134 | cylindrically-shaped section |
| 135 | proximal end |
| 136 | internally threaded bore |
| 137 | flat annular surface |
| 138 | flat annular surface |
| 139 | flat annular surface |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of implanting trial femoral and trial tibial knee prosthesis components comprising the steps of:

a) forming a plurality of surgical cuts on the patient's distal femur;

b) fitting a femoral trial prosthesis to the surgically prepared distal femur, the femoral trial prosthesis having a femoral articulating surface and a non-articulating surface that fits the patient's distal femur at the surgical cuts;

c) forming a transverse cut on the patient's proximal tibia;

d) placing a tibial trial prosthesis on the patient's proximal tibia, said tibial trial prosthesis including a tibial stem that fits the patient's intramedullary canal, a metallic tibial tray, and a plastic trial insert that fits the tibial tray said plastic insert having a tibial articulating surface that articulates with the femoral articulating surface;

e) placing the femoral articulating surface against the tibial articulating surface;

f) moving the patient's tibia through a range of motion during which the femoral and tibial articulating surfaces articulate with each other;

g) rotating the tibial trial prosthesis about its stem with an instrument that engages the plastic insert and wherein the instrument can be used to remove the plastic insert thus allowing replacement with another insert of a different size;

h) wherein articulation of the femoral trial prosthesis and tibial trial prosthesis in step "f" can be observed by the surgeon during the surgical procedure when the patient's tibia is moved through a range of motion relative to the patient's femur; and i) wherein in step "h" the trial tibial prosthesis is moved into different rotational trial positions.

2. The method of claim 1 wherein step "a" comprises forming surgical cuts on the distal femur that include at least anterior and posterior cuts that are generally parallel.

3. The method of claim 1 wherein step "a" comprises forming surgical cuts on the distal femur that include anterior and posterior cuts and a distal cut.

4. The method of claim 3 further comprising in step "a" forming said distal cut generally perpendicular to the anterior and posterior cuts.

5. The method of claim 3 further comprising in step "a" forming said distal cut generally perpendicular to the anterior and posterior cuts and chamfer cuts extending respectively between the distal cut and the anterior and posterior cuts, forming an acute angle with the distal cut.

6. The method of claim 1 further comprising the step between steps "e" and "f" of attaching an instrument to a slot on the plastic implant of the tibial prosthesis that enables the surgeon to manipulate the trial tibial prosthesis during an articulation of the tibial and femoral articulating surfaces and while the surgeon moves the tibia through a range of motion with respect to the femur.

7. The method of claim 1 wherein in step "d" the trial prosthesis includes a plurality of interchangeable tibial trays and a plurality of tibial stems and further comprising the step of sizing a trial tibial prosthesis by assembling a selected one of the trays to fit the patient's surgically prepared proximal tibia and a selected stem to fit the patient's tibial intramedullary canal.

8. A method of implanting a trial knee implant that includes corresponding trial femoral and trial tibial knee prosthesis components comprising the steps of:

a) forming a plurality of surgical cuts on the patient's distal femur;

b) fitting a femoral trial prosthesis to the surgically prepared distal femur, the trial prosthesis having a femoral articulating surface;

c) forming a transverse cut on the patient's proximal tibia;

d) building a tibial trial prosthesis for placement on the patient's proximal tibia, said tibial trial prosthesis being constructed from a selected one of the plurality of trays, a selected stem and a selected insert including a selected tibial stem that fits the patient's intramedullary canal, a selected metallic tibial tray, and a selected plastic trial insert having a tibial articulating surface;

e) placing the trial tibial prosthesis on the patient's proximal tibia;

f) placing the femoral articulating surface against the tibial articulating surface;

g) attaching a lever to the plastic insert;

h) moving the patient's tibia through a range of motion during which the femoral and tibial articulating surfaces articulate with each other;

i) rotating the tibial trial prosthesis about its stem so that articulation of the femoral trial prosthesis and tibial trial prosthesis can be obtained by the surgeon during the surgical procedure when:

1) the patient's tibia is moved through a range of motion; and 2) the trial tibial prosthesis is moved into different rotational trial positions using the lever.

9. The method of claim 8 further comprising the step between steps "g" and "h" of attaching the lever to a slot on the trial tibial prosthesis insert for enabling the surgeon to rotate the trial tibial prosthesis about its stem.

10. The method of claim 8 wherein step "a" comprises forming surgical cuts on the distal femur that include anterior and posterior cuts and a distal cut.

11. The method of claim 8 further comprising in step "a" forming a distal cut and anterior and posterior cuts generally perpendicular to said distal cut and chamfer cuts extending respectively between the distal cut and the anterior and posterior cuts.

12. The method of claim 8 further comprises attaching a lever with a handle to the plastic insert of the tibial prosthesis.

13. The method of claim 8 further comprising the step of forming a guide disconnect attachment between the lever and trial prosthesis. different rotational trial positions using the lever.

* * * * *